(12) United States Patent
Kang et al.

(10) Patent No.: US 7,528,276 B2
(45) Date of Patent: May 5, 2009

(54) PROCESS FOR PREPARING THE INTERMEDIATE COMPOUNDS FOR PPAR α LIGANDS

(75) Inventors: Heonjoong Kang, Seongnam-si (KR); Jungyeob Ham, Seoul (KR)

(73) Assignee: Seoul National University Industry Foundation (KR)

( * ) Notice: Subject to any disclaimer, the term of this patent is extended or adjusted under 35 U.S.C. 154(b) by 0 days.

(21) Appl. No.: 11/573,245

(22) PCT Filed: Sep. 26, 2005

(86) PCT No.: PCT/KR2005/003193

§ 371 (c)(1),
(2), (4) Date: Jun. 9, 2008

(87) PCT Pub. No.: WO2006/080652

PCT Pub. Date: Aug. 3, 2006

(65) Prior Publication Data

US 2008/0269516 A1  Oct. 30, 2008

(30) Foreign Application Priority Data

Oct. 5, 2004  (KR) .................. 10-2004-0078951

(51) Int. Cl.
C07C 229/00 (2006.01)
C07C 303/00 (2006.01)
C07C 321/00 (2006.01)
(52) U.S. Cl. .................. 560/37; 560/12; 560/17
(58) Field of Classification Search ............. 560/12, 560/17, 37
See application file for complete search history.

(56) References Cited

U.S. PATENT DOCUMENTS 6,306,854 B1  10/2001  Brown et al.

FOREIGN PATENT DOCUMENTS

| KR | 20030059175 | 7/2003 |
| KR | 1020030059175 A | 7/2003 |
| WO | 00/23407 | 4/2000 |
| WO | 0023407 | 4/2000 |
| WO | 02/28821 | 4/2002 |

OTHER PUBLICATIONS

International Search Report; PCT/KR2005/003193; Dec. 26, 2005. All references cited in the Search Report are listed in this IDS.
A Ureido-Thioisobutyric Acid (GW9578) Is a Subtype-Selective PPARa Agonist with Potent Lipid-Lowering Activity; Peter J. Brown, Deborah A. Winegar, Kelli D. Plunket, Linda B. Moore, Michael C. Lewis, Joan G. Wilson, Scott S. Sundseth, Cecilia S. Koble, Zhengdong Wu, James M. Chapman, Jurgen M. Lehmann, Steven A. Kliewer, Timothy M. Willson; J. Med Chem. 1999, 42, 3785-3788I.
Identification of a Subtype Selective Human PPARa Agonist Through Parallel-Array Synthesis; Peter J. Brown, L. William Stuarat, Kevin P. Hurley, Michael C. Lewis, Deborah A. Winegar, Joan G. Wilson, William O. Wilkison, Olivia R. Ittoop, Timothy M. Willson; Bioorganic & Medicinal Chemistry Letters 11 (2000) 1225-1227.

*Primary Examiner*—Jafar Parsa
(74) *Attorney, Agent, or Firm*—Cantor Colburn LLP

(57) ABSTRACT

The present invention provides a process for preparing the compounds of formula (II) according to a single reaction, which is an important intermediate compound for synthesizing GW7647 (III) and GW9578 (IV) activating Peroxisome Proliferator Activated Receptor (hPPAR α).

1 Claim, No Drawings

PROCESS FOR PREPARING THE INTERMEDIATE COMPOUNDS FOR PPAR α LIGANDS

TECHNICAL FIELD

The present invention relates to a process for preparing tert-butyl 2-[4-(2-aminoethyl)phenylthio]-2-methylpropionate of formula (II), which is an important intermediate compound for preparation of Ureidothioisobutylic acid (hereinafter, called to "Ureido-TiBA") derivatives activating Peroxisome Proliferator Activated Receptor (hPPAR α).

BACKGROUND ART

Especially, among Ureido-TiBA derivatives synthesized from the compounds of formula (II), 2-(4-{2-[3-cyclohexyl-1-(4-cyclohexylbutyl)ureido]ethyl}phenylthio)-2-methyl-propionic acid (hereinafter, called to "GW7647") and 2-(4-{2-[1-heptyl-3-(2,4-difluorophenyl)ureido]ethyl}phenyl-thio)-2-methyl propionic acid (hereinafter, called to "GW9578") are known as remedies for heart diseases caused by hypertension, high-cholesterol and an excess of fat (*J. Med. Chem.* 1999, 42, 3785; PCT publication WO 00/23407; *Bioorg Med. Chem. Lett.* 2001, 11, 1225). These articles disclosed the compounds of formula (II) for preparing Ureido-TiBA derivatives and the process for preparing the same.

Reaction scheme

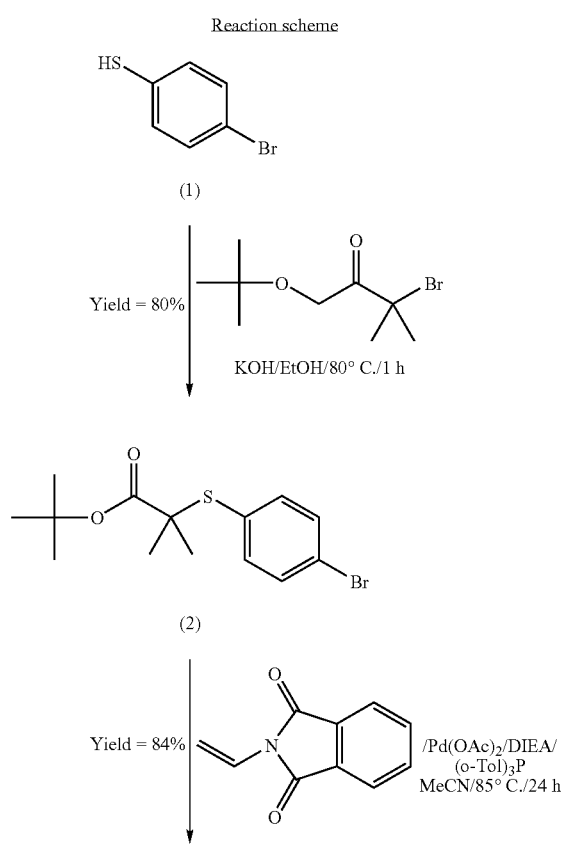

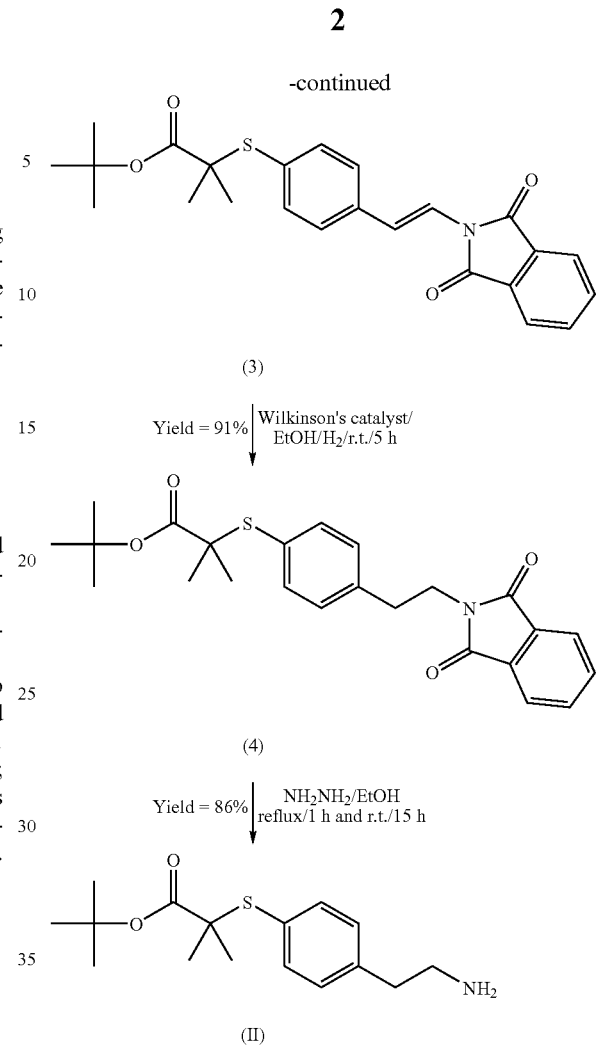

As above, tert-butyl 2-[4-(2-aminoethyl)phenylthio]-2-methylpropionate was obtained in 86% yield by reacting 4-bromothiophenol (1) as a starting material with tert-butyl 2-bromoisobutyrate to obtain tert-butyl 2-(4-bromophenylthio)-2-methylpropionate (2) in 80% yield, reacting it with N-vinyl phthalimide in presence of palladium catalyst for 24 hours to obtain tert-butyl 2-[4-(2-phthalimidoethenyl)phenylthio]-2-methylpropionate (3) in 84% yield, reducing the resulted compound (3) under Wilkinson catalyst to obtain tert-butyl 2-[4-(2-phthalimidoethyl)phenylthio]-2-methylpropionate (4) in 91% yield and then reacting the resulted compound (4) with hydrazine.

Although the above compound (II) has known to be an excellent efficacy, the manufacturing method thereof was not satisfactory, thereby being not cost-effective. That is to say, 1) The manufacturing method according to the reaction scheme consists of 4 steps, and the total yield thereof is as low as 53%. So, it is not proper to be applied to the industry.

2) The manufacturing process according to the reaction scheme includes two steps for more than 10 hours, which takes long time to obtain the final product.

3) Palladium (Pd) and rhodium (Rh) used in the reaction scheme are expensive to increase manufacturing cost and may lead to pollution of environment.

Under the circumstance, the novel process for preparing the above compound with easiness and low cost has been demanded in the art.

DISCLOSURE OF THE INVENTION

Technical Problem

An object of the present invention is to provide a process for preparing the compound of formula (II) by which cost and time can be minimized and yield can be higher than that of the prior method.

Technical Solution

In view of the above situation, the inventors of the present invention have conducted extensive studies on the novel processes for preparing compounds of the following formula (II). As a result, the inventors have found that the said compounds can be prepared in a high yield and high purity by reacting 4-bromophenethylamine of formula (I) with Grignard reagents to form compounds of formula (V), substituting lithium metals for halogens of the resulted compound, reacting the resulted compound with sulfur to form compounds of formula (VII) and reacting the resulted compound with tert-butyl haloacetate or tert-butyl haloisobutyrate as shown in the following reaction scheme.

Example of —($C_1$-$C_4$) alkyl group represented by $R_3$ and $R_4$ includes methyl, ethyl, propyl, isopropyl, n-butyl, sec-butyl and tert-butyl.

Compound of formula (I), which is used as a starting material, is commercially available or can be synthesized easily by using known methods in the art.

ADVANTAGEOUS EFFECTS

According to the method of the present invention, tert-butyl 2-[4-(2-aminoethyl)phenylthio]-2-methylpropionate of formula (II), which is an important intermediate compound for synthesizing ureido thioisobutylic acid (Ureido-TiBA) derivatives activating Peroxisome Proliferator Activated Receptor (hPPAR α), can be prepared in a high yield easily.

BEST MODE FOR CARRYING OUT THE INVENTION

The process of the present invention will be described as set below.

Preparation of Compounds of Formula (II):

Compounds of formula (II) can be prepared by synthesizing the intermediate compounds of formula (V), (VI) and (VII) from the compounds of formula (I) and reacting them with compounds of formula (VIII) sequentially without separation step.

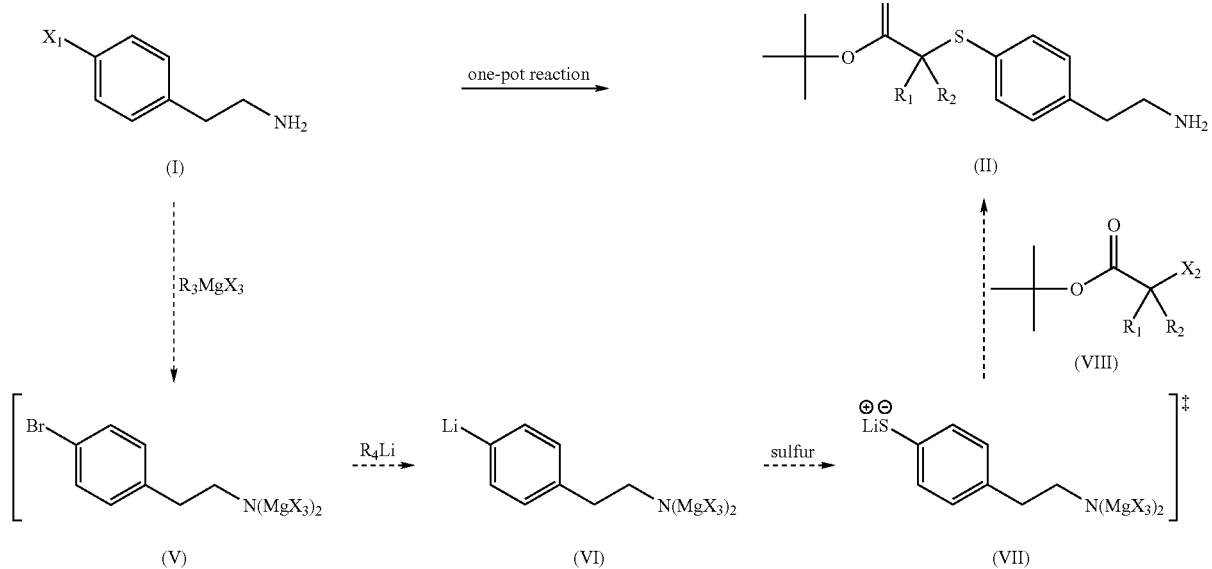

wherein, $R_1$ and $R_2$ represent methyl group or a hydrogen atom, $R_3$ and $R_4$ represent —($C_1$-$C_4$) alkyl group, $X_1$ represents a bromine atom or iodine atom, $X_2$ and $X_3$ represent a chlorine atom, bromine atom or iodine atom, An object of the present invention is to provide a process for preparing compounds of formula (II) by protecting amine of the compound of formula (I) with alkyl magnesium halide, reacting the resulted compound with organometallic reagents and sulfur ($S_8$) sequentially to form compounds of formula (VII), and reacting the resulted compounds with tert-butyl halogen acetate derivatives (VIII) and inorganic salts without separation step in the reaction.

Suitable anhydrous solvents usable in this reaction include diethyl ether, tetrahydrofuran, hexane, and heptane. These solvents may be used either singly or in combination of two or more. Of these, a solvent in combination of diethyl ether and tetrahydrofuran is preferred.

Suitable alkyl magnesium halide reagents usable in this reaction include $CH_3MgCl$, $CH_3MgBr$, $CH_3MgI$, $CH_3CH_2MgCl$, $CH_3CH_2MgBr$, $CH_3CH_2MgI$, $CH_3CH_2CH_2MgCl$, $CH_3CH_2CH_2MgBr$, $CH_3CH_2CH_2MgI$, $(CH_3)_2CHMgCl$, $(CH_3)_2CHMgBr$, $(CH_3)_2CHMgI$, $CH_3CH_2CH_2CH_2MgCl$, $CH_3CH_2CH_2CH_2MgBr$, $CH_3CH_2CH_2CH_2MgI$, $C_2H_5CHCH_3MgCl$, $C_2H_5CHCH_3MgBr$, $C_2H_5CHCH_3MgI$, $(CH_3)_3CMgCl$, $(CH_3)_3CMgBr$, $(CH_3)_3CMgI$. Of these, $R_3MgCl$ and R₃MgBr are preferred, (CH₃)₂CHMgCl and CH₃CH₂CH₂CH₂MgCl are more preferred.

As metal reagents used for halogen-metal substitution lithium metal or organometallic reagents such as n-butyl lithium, sec-butyl lithium, and tert-butyl lithium can be used. Of these, organometallic reagents are preferred and n-butyl lithium and tert-butyl lithium are more preferred.

A quantity of sulfur usable in this reaction is generally 0.5 to 2.0 eq. to compound of formula (I), with preferably 0.8 to 1.2 eq.

Tert-butyl chloroacetate derivatives (VIII) usable in this reaction include tert-butyl chloroacetate, tert-butyl bromoacetate, tert-butyl iodoacetate, tert-butyl 2-chloropropionate, tert-butyl 2-bromopropionate, tert-butyl 2-idodopropionate, tert-butyl chloroisobutyrate, tert-butyl bromoisobutyrate, tert-butyl iodoisobutyrate.

Suitable solvents usable in the reaction of compounds of formula (VIII) with the intermediate compounds of formula (VII) include single solvents such as methanol, ethanol, propanol, butanol, N,N-dimethylformamide (DMF) and dimethylsulfoxide, or organic solvents such as acetone and tetrahydrofuran (THF) including 5 to 10% water. Of these, methanol, ethanol, propanol and butanol are preferred, and methanol and ethanol are more preferred.

Inorganic salts usable in this reaction include lithium hydroxide, sodium hydroxide, potassium hydroxide, sodium bicarbonate, sodium carbonate and cesium carbonate. Of these, sodium hydroxide, potassium hydroxide and sodium carbonate are preferred, and sodium hydroxide, potassium hydroxide are more preferred.

The reaction temperature depends on the solvent to be used and the reaction steps. Generally, it is preferred to conduct the reaction at −100 to 85° C., more preferably in the step of the protection of amine groups at −10 to 20° C., in the steps of the halogen-metal substitution and the sulfur introduction at −75 to 40° C., and in the step of the reaction with the compounds of formula (VIII) at 30 to 85° C. The reaction time depends on the reaction temperature, the solvent to be used and the reaction steps. However, it is preferred to conduct the reaction for 30 minute to 1 day, more preferably within 2 hours.

EXAMPLES

The present invention will next be described in detail by way of examples, which should not be construed as limiting the invention.

Example 1

Preparation of
tert-butyl[4-(2-aminoethyl)phenylthio]acetate 4-bromophenethylamine (1.0 g, 5.0 mmol) was dissolved in anhydrous tetrahydrofuran (40 ml) in the presence of nitrogen and the reaction mixture was cooled to 0° C. At the same temperature, isopropyl magnesium chloride (5.0 ml, 10.0 mmol, 2.0 M ether solution, 2.0 eq.) was added slowly. After reaction for 15 minutes, the reaction mixture was cooled to −78° C. and tert-butyl lithium (6.5 ml, 11.0 mmol, 1.7 M hexane solution, 2.2 eq.) was added slowly for 1 minute. After further reaction at the same temperature for 1 hour, the solution of sulfur (162 mg, 5.0 mmol) in anhydrous tetrahydrofuran (5.0 ml) was added. The reaction mixture was heated to room temperature for 1 hour. After cooling the reaction mixture to 0° C., tert-butyl bromoacetate (738 µl, 5.0 mmol) was added. After further reaction at room temperature for 1 hour, the solvent was evaporated under reduced pressure and extracted by aqueous ammonium chloride solution (30 ml) and ethylacetate (3×25 ml). The resultant organic layer was dried over magnesium sulfate followed by filtration. The solvent was evaporated under reduced pressure and the resultant residue was purified by silica gel column chromatography (dichloromethane solvent including 3% aqueous ammonia and 10% methanol) to thereby yield 1.26 g of the title compound (yield: 94%).

¹H-NMR (300 MHz, CDCl₃) 7.36 (d, 2H, J=8.1 Hz), 7.13 (d, 2H, J=8.1 Hz), 3.53 (s, 2H), 2.95 (t, 2H, J=6.9 Hz), 2.71 (t, 2H, J=6.9 Hz), 1.40 (s, 9H), 1.31 (br s, 2H).

¹³C-NMR (75.5 MHz, CDCl₃) 169.3, 139.2, 130.9, 129.8, 120.4, 82.2, 43.9, 40.1, 38.5, 28.3.

Example 2

Preparation of
tert-butyl[4-(2-aminoethyl)phenylthio]acetate 4-bromophenethylamine (1.0 g, 5.0 mmol) was dissolved in anhydrous tetrahydrofuran (40 ml) in the presence of nitrogen and the reaction mixture was cooled to 0° C. At the same temperature, butyl magnesium chloride (5.0 ml, 10.0 mmol, 2.0 M ether solution, 2.0 eq.) was added slowly. After reaction for 15 minutes, the reaction mixture was cooled to −78° C. and tert-butyl lithium (6.5 ml, 11.0 mmol, 1.7 M hexane solution, 2.2 eq.) was added slowly for 1 minute. After further reaction at the same temperature for 1 hour, the solution of sulfur (162 mg, 5.0 mmol) in anhydrous tetrahydrofuran (5.0 ml) was added. The reaction mixture was heated to room temperature for 1 hour. After cooling the reaction mixture to 0° C., tert-butyl bromoacetate (738 µl, 5.0 mmol) was added. After further reaction at room temperature for 1 hour, the solvent was evaporated under reduced pressure and extracted by aqueous ammonium chloride solution (30 ml) and ethylacetate (3×25 ml). The resultant organic layer was dried over magnesium sulfate followed by filtration. The solvent was evaporated under reduced pressure and the resultant residue was purified by silica gel column chromatography (dichloromethane solvent including 3% aqueous ammonia and 10% methanol) to thereby yield 1.24 g of the title compound (yield: 93%).

Example 3

Preparation of
tert-butyl[4-(2-aminoethyl)phenylthio]acetate 4-bromophenethylamine (1.0 g, 5.0 mmol) was dissolved in anhydrous tetrahydrofuran (40 ml) in the presence of nitrogen and the reaction mixture was cooled to 0° C. At the same temperature, isopropyl magnesium chloride (5.0 ml, 10.0 mmol, 2.0 M ether solution, 2.0 eq.) was added slowly. After reaction for 15 minutes, the reaction mixture was cooled to −78° C. and tert-butyllithium (6.5 ml, 11.0 mmol, 1.7 M hexane solution, 2.2 eq.) was added slowly for 1 minute. After further reaction at the same temperature for 1 hour, the solution of sulfur (162 mg, 5.0 mmol) in anhydrous tetrahydrofuran (5.0 ml) was added. The reaction mixture was heated to room temperature for 1 hour. After cooling the reaction mixture to 0° C., tert-butyl chloroacetate (715 µl, 5.0 mmol) was added. After further reaction at room temperature for 1 hour, the solvent was evaporated under reduced pressure and extracted by aqueous ammonium chloride solution (30 ml) and ethylacetate (3×25 ml). The resultant organic layer was dried over magnesium sulfate followed by filtration. The solvent was evaporated under reduced pressure and the resultant residue was purified by silica gel column chromatography (dichloromethane solvent including 3% aqueous ammonia and 10% methanol) to thereby yield 1.16 g of the title compound (yield: 87%).

Example 4

Preparation of tert-butyl 2[4-(2-aminoethyl)phenylthio]-2-methylpropionate 4-bromophenethylamine (1.290 g, 6.5 mmol) was dissolved in anhydrous tetrahydrofuran (50 ml) in the presence of nitrogen and the reaction mixture was cooled to 0° C. At the same temperature, isopropyl magnesium bromide (6.5 ml, 13.0 mmol, 2.0 M ether solution, 2.0 eq.) was added slowly. After reaction for 15 minutes, the reaction mixture was cooled to −78° C. and tert-butyl lithium (8.4 ml, 14.3 mmol, 1.7 M hexane solution, 2.2 eq.) was added slowly for 1 minute. After further reaction at the same temperature for 1 hour, the solution of sulfur (208 mg, 6.5 mmol) in anhydrous tetrahydrofuran (6.0 mH) was added. The reaction mixture was heated to room temperature slowly. After 1 hour, the solvents are evaporated under reduced pressure and ethanol (32 ml) was added. Calcium hydroxide (352 mg, 6.5 mmol) and tert-butyl 2-bromoisobutyrate (1.21 ml, 6.5 mmol) were added sequentially. The reaction mixture was reacted at 80° C. for 1 hour with refluxing. After cooling the reaction mixture to room temperature, the solvent was evaporated under reduced pressure and extracted by aqueous ammonium chloride solution (40 ml) and ethylacetate (3×25 ml). And the resultant organic layer was dried over magnesium sulfate. After filtration, the solvent was evaporated under reduced pressure and the resultant residue was purified by silica gel column chromatography (dichloromethane solvent including 3% aqueous ammonia and 10% methanol) to thereby yield 1.77 g of the title compound (yield: 92%).

$^1$H-NMR (300 MHz, CDCl$_3$) 7.45 (d, 2H, J=8.0 Hz), 7.16 (d, 2H, J=8.0 Hz), 2.97 (t, 2H, J=7.0 Hz), 2.76 (t, 2H, J=7.0 Hz), 1.44 (s, 6H), 1.43 (s, 9H), 1.32 (br s, 2H).

$^{13}$C-NMR (75.5 MHz, CDCl$_3$) 173.5, 141.5, 137.4, 129.8, 129.4, 129.2, 128.9, 81.3, 51.7, 43.8, 40.2, 28.3, 26.5.

HREIMS: C$_{16}$H$_{25}$NO$_2$S
Calculated value 295.1606
Measured value 295.1605

Example 5

Preparation of tert-butyl 2[4-(2-aminoethyl)phenylthio]-2-methylpropionate 4-iodophenethylamine (300 mg, 1.2 mmol) was dissolved in anhydrous tetrahydrofuran (10 ml) in the presence of nitrogen and the reaction mixture was cooled to 0° C. At the same temperature, isopropyl magnesium bromide (1.2 ml, 2.4 mmol, 2.0 M ether solution, 2.0 eq.) was added slowly. After reaction for 15 minutes, the reaction mixture was cooled to −78° C. and tert-butyl lithium (1.6 ml, 2.6 mmol, 1.7 M hexane solution, 2.2 eq.) was added slowly for 1 minute. After further reaction at the same temperature for 1 hour, the solution of sulfur (38 mg, 1.2 mmol) in anhydrous tetrahydrofuran (2.0 ml) was added. The reaction mixture was heated to room temperature slowly. After 30 minutes, the solvents are evaporated under reduced pressure and ethanol (10 ml) was added. Sodium hydroxide (48 mg, 1.2 mmol) and tert-butyl 2-bromoisobutyrate (224 μl, 1.2 mmol) were added sequentially. The reaction mixture was reacted at 80° C. for 40 minutes with refluxing. After cooling the mixture to room temperature, the solvent was evaporated under reduced pressure and extracted by aqueous ammonium chloride solution (15 ml) and ethylacetate (3×15 ml). And the resultant organic layer was dried over magnesium sulfate. After filtration, the solvent was evaporated under reduced pressure and the resultant residue was purified by silica gel column chromatography (dichloromethane solvent including 3% aqueous ammonia and 10% methanol) to thereby yield 320 mg of the title compound (yield: 90%).

INDUSTRIAL APPLICABILITY

As described above, according to the present invention, tert-butyl 2-[4-(2-aminoethyl)phenylthio]-2-methylpropionate of formula (II), which is an important intermediate compound for synthesizing ureido thioisobutylic acid (Ureido-TiBA) derivatives activating Peroxisome Proliferator Activated Receptor (hPPAR α), can be prepared in a high yield easily.

The invention claimed is:

1. A process for preparing intermediate compounds of formula (II) for preparing ligands of PPAR α which comprises reacting 4-bromophethylamine of formula (I) with Grignard reagents to form compounds of formula (V), substituting lithium metal for halogen of said compounds of formula (V), reacting the resulted compounds with sulfur to form lithium-thiol intermediate compounds and reacting the resulted compounds with compounds of formula (VIII) continuously without separation and purification,

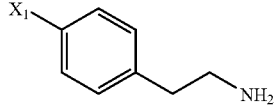
(I)

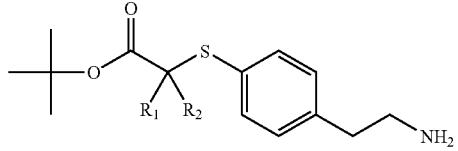
(II)

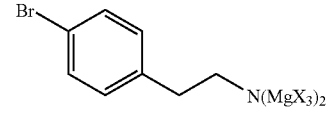
(V)

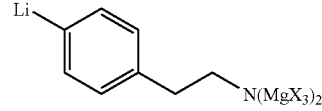
(VI)

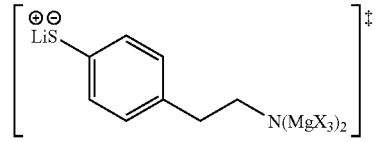
(VII)

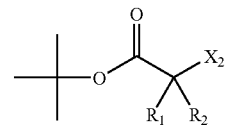
(VIII)

wherein,
R$_1$ and R$_2$ represent methyl group or a hydrogen atom,
R$_3$ of Grignard reagents (R$_3$MgX$_3$) and R$_4$ of alkyl lithium reagents (R$_4$Li) represent —(C$_1$-C$_4$) alkyl group,
X$_1$ represents a bromine atom or iodine atom,
X$_2$ and X$_3$ represent a chlorine atom, bromine atom or iodine atom.

* * * * *